US011534053B2

(12) United States Patent
Maichle et al.

(10) Patent No.: US 11,534,053 B2
(45) Date of Patent: Dec. 27, 2022

(54) OPTICAL INSTRUMENT

(71) Applicant: KARL STORZ SE & Co. KG, Tuttlingen (DE)

(72) Inventors: Stefanie Maichle, Tuttlingen (DE); Michael Egle, Tuttlingen (DE); Claus Kramer, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 831 days.

(21) Appl. No.: 16/196,361

(22) Filed: Nov. 20, 2018

(65) Prior Publication Data
US 2019/0159660 A1 May 30, 2019

(30) Foreign Application Priority Data
Nov. 24, 2017 (DE) ..................... 10 2017 127 827.3

(51) Int. Cl.
*A61B 1/00* (2006.01)
*G02B 23/24* (2006.01)

(52) U.S. Cl.
CPC ........ *A61B 1/00137* (2013.01); *A61B 1/0011* (2013.01); *A61B 1/00096* (2013.01);
(Continued)

(58) Field of Classification Search
CPC ............ A61B 1/00137; A61B 1/00096; A61B 1/0011; A61B 1/00165; A61B 1/00064; A61B 1/002; A61B 1/00163; A61B 2090/0813; G02B 7/028; G02B 27/0006; G02B 7/00; G02B 7/02; G02B 7/021; G02B 7/001; G02B 7/03; G02B 23/2423; G02B 23/2453; G02B 23/2476; B23K 1/002; B23K 1/008; B23K 1/012
See application file for complete search history.

(56) References Cited

U.S. PATENT DOCUMENTS 4,148,550 A * 4/1979 MacAnally ............ A61B 1/002
359/435
4,779,613 A * 10/1988 Hashiguchi ........ A61B 1/00179
359/512
(Continued)

FOREIGN PATENT DOCUMENTS

DE     195 07 205 C2    12/1996
DE     198 36 285 C1    10/1999
(Continued)

*Primary Examiner* — Timothy J Neal
*Assistant Examiner* — Genja M Frankert
(74) *Attorney, Agent, or Firm* — McGlew and Tuttle, P.C.

(57) ABSTRACT

An optical instrument (1) for minimally invasive surgery includes an instrument housing (2) for receiving optical elements, wherein the instrument housing (2) is sealed in fluid tight fashion by way of at least one end window (7) on the distal side and/or proximal side. The end window (7) is arranged in a window frame (8) that surrounds the end window (7) around the entire circumference thereof. The end windows (7) is able to be attached with little stress in the associated window frame (8) based on at least two portions (12) that project radially to the inside from the window frame (8). The at least two portions (12) are formed on the inner circumferential surface of each window frame (8) facing the respective end window (7).

19 Claims, 2 Drawing Sheets

(52) U.S. Cl.
CPC ...... *A61B 1/00165* (2013.01); *G02B 23/2423* (2013.01); *G02B 23/2453* (2013.01); *G02B 23/2476* (2013.01)

(56) References Cited

U.S. PATENT DOCUMENTS

| | | | | |
|---|---|---|---|---|
| 5,536,244 | A * | 7/1996 | Muller | A61B 1/00096 228/124.1 |
| 6,201,649 | B1 * | 3/2001 | Rudischhauser | G02B 7/025 359/808 |
| 6,246,823 | B1 | 6/2001 | Kraas et al. | |
| 6,398,723 | B1 * | 6/2002 | Kehr | A61B 1/002 359/435 |
| 6,525,888 | B2 * | 2/2003 | Schletterer | G02B 7/023 359/813 |
| 2002/0128535 | A1 | 9/2002 | Kikuchi | A61B 1/0011 600/101 |
| 2002/0186478 | A1 * | 12/2002 | Watanabe | G02B 7/02 359/819 |
| 2004/0176662 | A1 * | 9/2004 | Forkey | A61B 1/002 600/133 |
| 2007/0171550 | A1 * | 7/2007 | Kuroda | G02B 7/02 359/811 |
| 2008/0062540 | A1 * | 3/2008 | Scholer | G02B 7/02 359/819 |
| 2010/0199448 | A1 * | 8/2010 | Vazales | A61B 90/70 15/104.05 |
| 2012/0176669 | A1 * | 7/2012 | Kiedrowski | A61B 1/0011 359/362 |
| 2013/0027534 | A1 * | 1/2013 | Kibayashi | G02B 7/10 348/65 |
| 2014/0275786 | A1 * | 9/2014 | Goto | G02B 23/2476 600/133 |
| 2015/0065796 | A1 * | 3/2015 | Iwane | B23K 1/012 600/109 |
| 2017/0064164 | A1 * | 3/2017 | Nishihara | A61B 1/005 |
| 2018/0098688 | A1 * | 4/2018 | Ogawa | A61B 1/002 |

FOREIGN PATENT DOCUMENTS

| | | |
|---|---|---|
| DE | 197 50 685 C2 | 8/2003 |
| EP | 1031054 B1 | 8/2000 |
| EP | 3225149 A1 | 10/2017 |

\* cited by examiner

OPTICAL INSTRUMENT

CROSS REFERENCE TO RELATED APPLICATIONS

This application claims the benefit of priority under 35 U.S.C. § 119 of German Application 10 2017 127 827.3, filed Nov. 24, 2017, the entire contents of which are incorporated herein by reference.

TECHNICAL FIELD

The invention relates to an optical instrument for minimally invasive surgery, comprising an instrument housing for receiving optical elements, wherein the instrument housing is sealed in fluid tight fashion by way of at least one end window on the distal side and/or proximal side, said end window being arranged in a window frame that surrounds the end window around the entire circumference thereof.

BACKGROUND

Endoscopes and other medical optical instruments for minimally invasive surgery have to be sterilized prior to each use. These days, this sterilization is implemented by autoclaving, in which the optical instruments are exposed to treatment with hot vapor at over 3 bar pressure and a temperature of more than 130° C.

A generic optical instrument for minimally invasive surgery is known from DE 195 07 205 C2, for example.

In order to ensure that no moisture penetrates into the instrument housing, even in the case of the high thermal loads during autoclaving, the practice of connecting the end side end windows, which are used as cover glasses and/or end lenses, to the instrument housing in fluid tight fashion by welding or soldering has been disclosed.

In order to solder the end windows into the corresponding window frame of the instrument housing, the end windows have a metallic edge coating, as a result of which they can be soldered into the window frame provided therefor using tin or gold solder. When soldering into the window frame, the respective end window is surrounded by a liquid solder bath. In this position, in which the end window virtually swims in the solder bath, it is difficult to arrange the end window exactly centrally in the window frame. Then, an off centered position of the end window automatically leads to a solder layer of varying thickness between the end window and the window frame.

On account of different coefficients of thermal expansion of the employed materials in the instrument housing, the window frame and the solder, significant stresses arise again and again, particularly in the case of the off centered placement of the end windows in the window frame, this may lead to the formation of tears and/or stress fractures at the end windows, and hence to leaks.

SUMMARY OF THE INVENTION

The invention is based on an object of developing an optical instrument for minimally invasive surgery, in which the end windows are able to be attached with little stress in the associated window frame.

According to the invention, this object is achieved by virtue of at least two portions that project radially to the inside from the window frame being formed on the inner circumferential surface of each window frame facing the respective end window.

As a result of forming individual separate portions that project radially to the inside from the window frame, the respective end window is held centrally in the window frame during soldering since there remains hardly any space for an off centered displacement of the end window on account of the portions that project radially to the inside. Consequently, this embodiment allows a solder edge that has a substantially uniform thickness to be formed over the entire circumference of the end window to be soldered. Stress on the respective end window occurring during soldering and cooling can be significantly reduced by way of this uniformly thick solder edge around the respective end window, and so stress tears or stress fractures no longer occur at the end windows.

Three or four portions that project radially to the inside being formed on each window frame is proposed by a preferred embodiment of the invention.

Forming three or four portions that project radially to the inside was found to be particularly effective for ensuring a central placement of the end window in the respective window frame and, secondly, for providing sufficient clear space for the formation of the substantially uniformly thick solder edge.

Naturally, the provision of more than four portions that project radially to the inside on the associated window frame is also possible according to the invention.

Further, a gap for forming a solder layer being embodied between the radial inner surfaces of the portions of each window frame that project radially to the inside and the associated end window is proposed by the invention. This remaining gap between the window frame and the end window ensures the formation of the solder edge which surrounds the end window over the entire circumference thereof and which ensures the fluid tight seal.

In relation to the embodiment of the portions that project radially to the inside, each portion that projects radially to the inside from the window frame being embodied as a wave shaped protrusion is proposed according to the invention.

A virtually only punctiform embodiment of the region in which the solder edge between the window frame and the end window has a particularly thin embodiment emerges on account of the wave shaped protrusion.

Firstly, the wave shaped embodiment of the portions of the window frame that project radially to the inside is sufficient for placing the end window centrally in the window frame and, secondly, this ensures the formation of a substantially uniformly thick solder edge, as a result of which the formation of possible stresses on account of different coefficients of thermal expansion of the employed materials is significantly reduced.

In order to ensure a central position of the end windows in the associated window frame, all wave shaped protrusions of a window frame having the same radius of curvature is proposed by the invention. In the case of an optical instrument with a plurality of end windows, it is self evident that the radii of curvature of the wave shaped protrusions of each window frame may differ from the radii of curvature of the other window frames of the same optical instrument.

According to the invention, the occurrence of possible stresses on account of different coefficients of thermal expansion of the employed materials can be further reduced by virtue of the portions that project radially to the inside being arranged in uniformly distributed fashion over the inner circumference of the respective window frame. By way of example, if three portions are used, these are arranged offset by 120°, and, if four portions are used, these are arranged offset by 90°, in relation to one another in a manner distributed over the inner circumference of the window frame.

The distal and/or proximal end of the instrument housing forming the window frame is proposed by the invention for the purposes of embodying the window frames for receiving the end windows. This direct embodiment of the distal and/or proximal housing inner wall as a window frame is used, in particular, in the case of optical instruments with a small shaft diameter, for example of less than 10 mm.

Finally, the window frame being embodied as a separate component that is attachable to the distal and/or proximal end of the instrument housing is proposed by an alternative embodiment of the invention. This embodiment of the window frame as a separate component, which is attachable to the distal and/or proximal housing inner wall, is used, in particular, in the case of optical instruments with a relatively large shaft diameter, for example of 10 mm and more.

Further features and advantages of the invention emerge from the associated drawings, in which an exemplary embodiment of an optical instrument according to the invention for minimally invasive surgery is illustrated purely in exemplary fashion, without restricting the invention to this exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
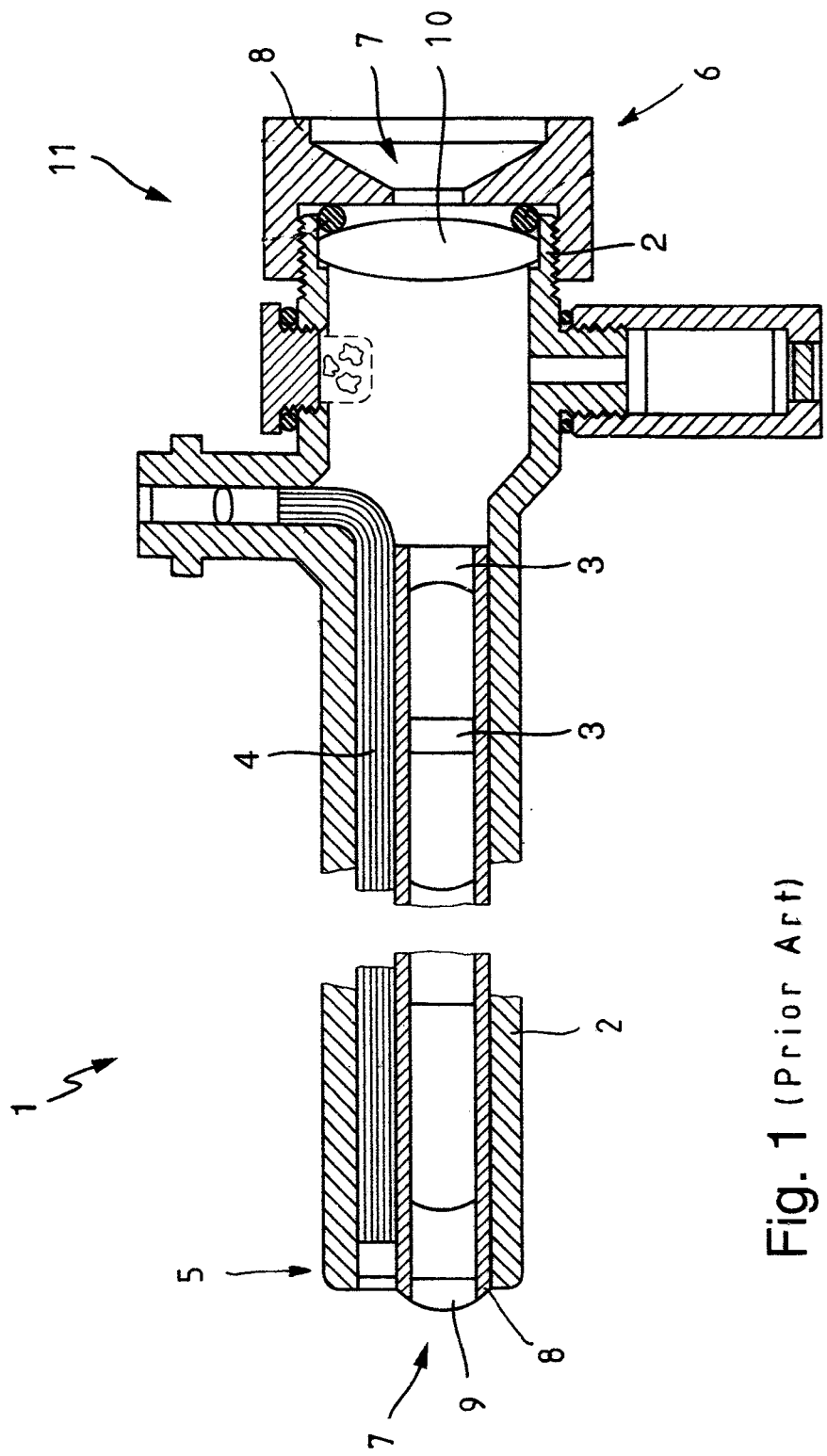
FIG. 1 is a schematic longitudinal sectional view through an optical instrument for minimally invasive surgery, embodied as an endoscope, according to the prior art.

Referring to the drawings, FIG. 1 schematically shows the structure of an optical instrument 1 for minimally invasive surgery, embodied as an endoscope. The optical instrument 1 has a hollow instrument housing 2, in which various optical elements, such as lenses 3 and an optical fiber bundle 4, for example, are arranged.

At a distal end 5 and at a proximal end 6, the instrument housing 2 is sealed in fluid tight fashion by way of an end window 7 in each case, this end window being arranged in a window frame 8 that surrounds the end window 7 around the entire circumference thereof.

In the optical instrument 1 illustrated in FIG. 1, the distal side end window 7 is embodied as an end lens 9 and the proximal side end window 7 is embodied as a cover glass 10 in an eyepiece unit 11.

Endoscopes and other medical optical instruments 1 have to be sterilized prior to each use. These days, this sterilization is implemented by autoclaving, in which the optical instruments 1 are exposed to treatment with hot vapor at over 3 bar pressure and a temperature of more than 130° C.

In order to ensure that no moisture penetrates into the instrument housing 2, even in the case of the high thermal loads during autoclaving, the end side end windows 7, which are used as cover glasses 10 and/or end lenses 9, are connected to the instrument housing 2 in fluid tight fashion by, in particular, thermal bonding processes, such as welding or soldering. As a rule, adhesive bonding processes are not suitable for the insertion of the end windows 7 since the adhesive bonds do not withstand the thermal loads of autoclaving in the long run.

Significant stresses may occur when autoclaving the optical instruments 1 on account of different coefficients of thermal expansion of the employed materials in the case of end windows 7 that are welded or soldered to the instrument housing 2, it being possible that these stresses lead to the formation of tears and/or stress fractures in the end windows 7, and hence to leaks.

In optical instruments 1 according to the prior art, these stresses may occur on account of the respective end window 7 being surrounded by a liquid solder bath and only being affixed by a solder mandrel when being soldered into the window frame 8. For the purposes of soldering the end windows 7 into the corresponding window frame 8 of the instrument housing 2, the end windows 7 have a metallic edge coating, as a result of which they can be soldered into the window frame 8 provided therefor using tin or gold solder.

In this position, in which the end window 7 virtually swims in the solder bath, it is difficult to arrange the end window 7 exactly centrally in the window frame 8, particularly in the case of angled optical units. An offcentered position of the end window 7 then automatically leads to a solder layer with varying thickness between the end window 7 and the window frame 8, and so different thermal expansions may occur during soldering and thermal compressions may occur during the subsequent cooling.

In principle, two different embodiments are available for forming the window frames 8 for receiving the end windows 7.

Preferably, in the case of optical instruments 1 with a small shaft diameter of the instrument housing 2, for example a diameter of less than 10 mm, the housing inner wall of the instrument housing 2, particularly at the distal end 5 of the instrument housing 2, directly forms the window frame 8.

Figure 2:
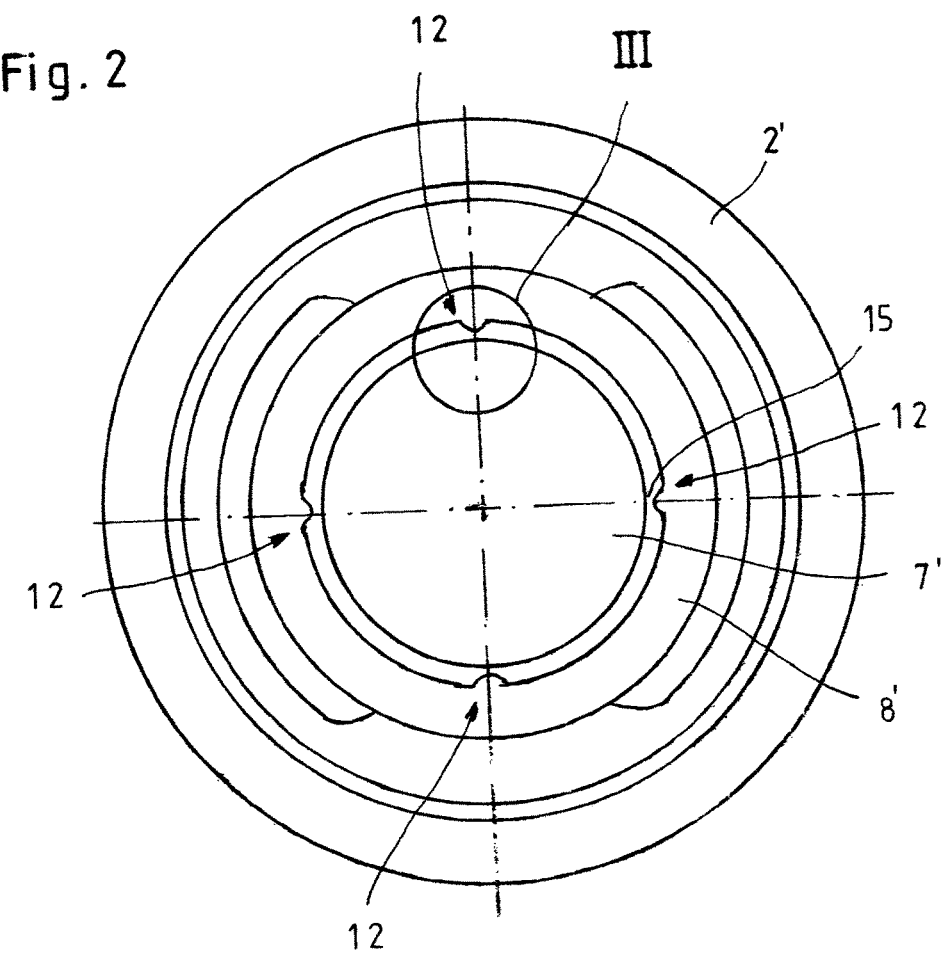
FIG. 2 is a cut front view of a distal end of an optical instrument according to the invention.

In the case of optical instruments 1 with a relatively large shaft diameter of the instrument housing 2, for example 10 mm and more, the window frame 8 is embodied as a separate component, in particular at the distal end 5 of the instrument housing 2, it being possible to attach said separate component to the distal housing inner wall of the instrument housing 2, as illustrated in FIG. 2.

The structure of the window frame 8', according to the invention, is explained below on the basis of FIGS. 2 and 3.

In order to develop an optical instrument in which the end windows 7' are able to be attached with little stress in the associated window frame 8', at least two portions 12 project radially to the inside from the window frame 8' (project radially to an inside with respect to adjacent portions of the inner circumferential surface of the window frame 8). The at least two portions 12 are formed on the inner circumferential surface of each window frame 8' facing the respective end window 7'.

Figure 3:
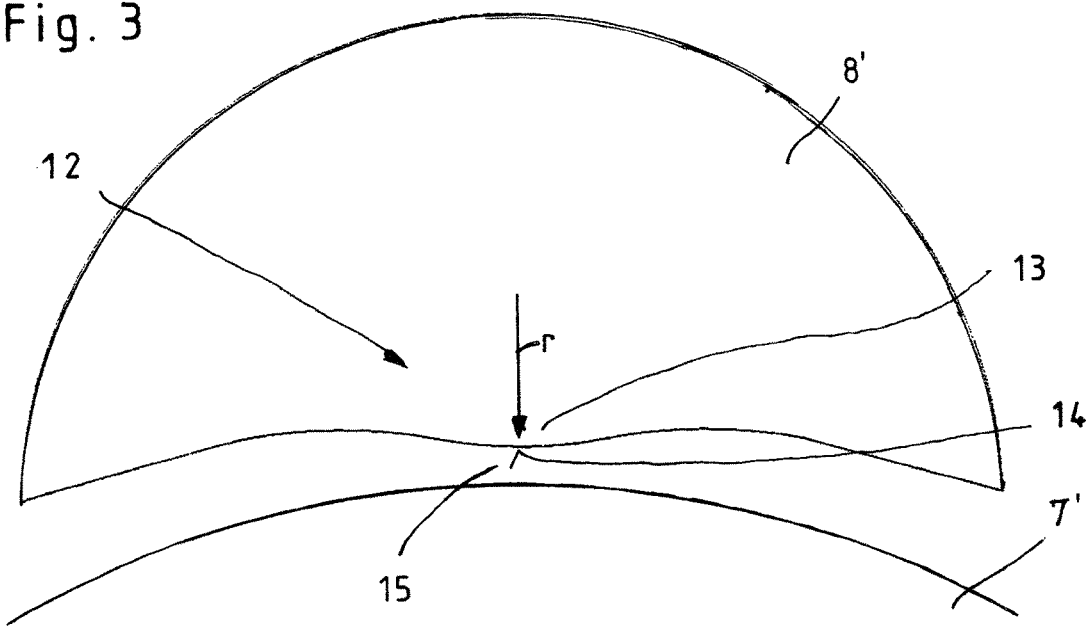
FIG. 3 is a magnified illustration of the detail III according to FIG. 2.

As is clear from FIG. 3, in particular, the portions 12 that project radially to the inside are preferably embodied as wave shaped protrusions 13 of the window frame 8'. The radial height of the portions 12 that project to the inside is dimensioned in such a way that a gap 15 for forming a solder layer remains between the radial inner surfaces 14 of the portions 12 of each window frame 8' that project radially to the inside and the associated end window 7'.

As a result of forming individual separate portions 12 that project radially to the inside from the window frame 8', the respective end window 7' is held centrally in the window frame 8' during soldering since there remains hardly any space for an off centered displacement of the end window 7' on account of the portions 12 that project radially to the inside and on account of the only small gap 15 between the radial inner surfaces 14 of the portions 12 and the outer circumference of the end window 7'. Consequently, this embodiment allows a solder edge that has a substantially uniform thickness to be formed over the entire circumference of the end window 7' to be soldered. Stress on the respective end window 7' occurring during soldering and cooling can be significantly reduced by way of this uniformly thick solder edge around the respective end window 7', and so stress tears or stress fractures no longer occur at the end windows 7'.

In the embodiment illustrated in FIG. 2, the window frame has four portions 12 that project radially to the inside and that are embodied as wave shaped protrusions 13. Naturally, the provision of only three or more than four portions 12 that project radially to the inside at each window frame 8 is also possible.

In FIG. 2, the wave shaped protrusions 13 are illustrated with enlarged proportions in relation to the window frame 8' and the end window 7' and are not illustrated true to scale in order to be able to vividly present the embodiment of the portions 12 that project radially to the inside.

As is furthermore clear from FIG. 2, the four portions 12 that project radially to the inside are arranged in a manner distributed uniformly over the inner circumference of the window frame 8' and offset by 90° in relation to one another. The uniform distribution of the portions 12 that project radially to the inside over the inner circumference of the window frame 8', which is also advantageous with corresponding angular distances in the case of a different number of portions 12 that project radially to the inside, reduces the occurrence of stresses since this furthermore makes the embodiment of the solder edge uniform over the circumference of the end window 7'.

In order to ensure a central position of the end windows 7' in the associated window frame 8', all wave shaped protrusions 13 of one window frame 8' have the same radius of curvature r.

In the case of an optical instrument with a plurality of end windows 7', it is self evident that the radii of curvature r of the wave shaped protrusions 13 of each window frame 8' may differ from the radii of curvature r of the other window frames 8' of the same optical instrument 1.

A window frame 8' with window 7' of an optical instrument, which optical instrument is otherwise configured with features of the optical instrument 1 as described above, is consequently distinguished by the fact that, on account of the embodiment of the portions 12 that project radially to the inside from the window frame 8', the end window 7' to be soldered into the window frame 8' can always be placed centrally in the window frame 8'. At the same time, this ensures the formation of a substantially uniformly thick solder edge between the window frame 8' and the end window 7', as a result of which stress on the respective end window 7', occurring during soldering and cooling, can be significantly reduced, and so stress tears or stress fractures no longer occur at the end windows 7'.

While specific embodiments of the invention have been shown and described in detail to illustrate the application of the principles of the invention, it will be understood that the invention may be embodied otherwise without departing from such principles.

The invention claimed is:

1. An optical instrument for minimally invasive surgery, the optical instrument comprising:
    an instrument housing for receiving optical elements;
    at least one window frame;
    at least one end window, wherein the instrument housing is fluid-tight sealed by way of the at least one end window on one of a distal side and a proximal side, said end window being arranged in the at least one window frame and the at least one window frame surrounding the at least one end window around an entire circumference thereof, wherein the at least one window frame comprises an inner circumferential surface, facing the at least one end window, comprising at least two undulating portions that project radially to an inside the at least one window frame,
    wherein the inner circumferential surface extends continuously, without interruption, about the at least one end window, wherein the at least two undulating portions are in a permanent fixed position.

2. The optical instrument as claimed in claim 1, wherein the inner circumferential surface further comprises at least another portion that projects radially to the inside with respect to adjacent portions of the inner circumferential surface of the at least one window frame to provide three or four portions that project radially to the inside.

3. The optical instrument as claimed in claim 1, wherein each of the portions that project radially to the inside of the at least one window frame is embodied as an undulating protrusion.

4. The optical instrument as claimed in claim 3, wherein all undulating protrusions of the at least one window frame have a radius of curvature of a same value.

5. The optical instrument as claimed in claim 1, wherein the portions that project radially to the inside are arranged uniformly distributed over the inner circumference of the at least one window frame.

6. The optical instrument as claimed in claim 1, wherein a gap, for forming a solder layer, is embodied between radial inner surfaces of the portions of the at least one window frame that project radially to the inside and the at least one end window.

7. The optical instrument as claimed in claim 1, wherein an end of the instrument housing forms the at least one window frame.

8. The optical instrument as claimed in claim 1, wherein:
    the at least one window frame and the instrument housing are embodied as separate components; and
    the at least one window frame is attachable to a distal end or a proximal end of the instrument housing.

9. The optical instrument as claimed in claim 1, further comprising:
    another window frame; and
    another end window, wherein:
    the instrument housing is fluid-tight sealed by the another end window on another of the distal side and the proximal side;
    the another end window is arranged in the another window frame and the another window frame surrounds the another end window around an entire circumference thereof;

the another window frame comprises an inner circumferential surface, facing the another end window, comprising at least two portions that project radially to an inside with respect to adjacent portions of the inner circumferential surface of the another window frame.

10. The optical instrument as claimed in claim 9, wherein:
the instrument housing has a distal end and a proximal end;
the at least one window frame is at or adjacent to a proximal end of the instrument housing;
the at least one window frame and the instrument housing are embodied as separate components; and
the at least one window frame is attachable to the proximal end of the instrument housing.

11. The optical instrument as claimed in claim 9, wherein:
the instrument housing has a distal end and a proximal end;
the instrument housing forms the another window frame at one of the distal end and the proximal end of the instrument housing.

12. The optical instrument as claimed in claim 1, wherein the inner circumferential surface faces an outer circumferential surface of the at least one end window.

13. The optical instrument as claimed in claim 12, wherein the inner circumferential surface further comprises at least another portion that projects radially inward in the direction of the longitudinal axis of the instrument with respect to adjacent portions of the inner circumferential surface of the at least one window frame to provide three or four inner circumferential surface portions that project radially inward in the direction of the longitudinal axis.

14. The optical instrument as claimed in claim 13, wherein each of the portions that project radially to the inside from the at least one window frame comprises a protrusion.

15. The optical instrument as claimed in claim 14, wherein all protrusions of the at least one window frame have a radius of curvature of a same value.

16. The optical instrument as claimed in claim 12, wherein each of the at least two portions is located at a first distance from the end window and each of the at least two portions is located adjacent to another portion of the inner circumferential surface, the another portion being located a second distance from the end window, the first distance being less than the second distance.

17. The optical instrument as claimed in claim 12, wherein the at least two portions are arranged about an outer periphery of the end window.

18. The optical instrument as claimed in claim 17, wherein each of the at least two portions is located at a first distance from the end window and each of the at least two portions is located adjacent to another portion of the inner circumferential surface, the another portion being located a second distance from the end window, the first distance being less than the second distance.

19. The optical instrument as claimed in claim 17, wherein the inner circumferential surface further comprises at least another portion that projects radially inward in the direction of a longitudinal axis of the end window with respect to adjacent portions of the inner circumferential surface of the at least one window frame to provide three or four inner portions that project radially inward in the direction of the longitudinal axis.

* * * * *